US006106288A

United States Patent [19]
Brassil et al.

[11] Patent Number: 6,106,288
[45] Date of Patent: Aug. 22, 2000

[54] AIR ABRASION SYSTEM FOR USE IN DENTAL PROCEDURES

[75] Inventors: John Michael Brassil, Glenview; John Andrew Lake, Evanston, both of Ill.; Andrew C. Burroughs, Kenosha, Wis.; Stephen D. Barry, Plainfield; Shu Kun Chang, Evanston, both of Ill.; Roberto Giovanni Fraquelli, London; David Howard Meldrum Annett, Harrogate, both of United Kingdom

[73] Assignee: Dentsply Research & Development Corp., Los Angeles, Calif.

[21] Appl. No.: 08/953,109

[22] Filed: Oct. 17, 1997

[51] Int. Cl.$^7$ .................................................. A61C 3/02
[52] U.S. Cl. ................................................................ 433/88
[58] Field of Search ................................ 433/88; 451/90, 451/102

[56] References Cited

U.S. PATENT DOCUMENTS

| | | | |
|---|---|---|---|
| 2,661,537 | 12/1953 | Angell | 433/88 |
| 3,972,123 | 8/1976 | Black | 433/88 |
| 4,340,366 | 7/1982 | Heil | 433/82 |
| 4,412,402 | 11/1983 | Gallant | 51/439 |
| 4,482,322 | 11/1984 | Hain et al. | 433/88 |
| 4,487,582 | 12/1984 | Warrin | 433/88 |
| 4,492,575 | 1/1985 | Mabille | 433/88 |
| 4,733,503 | 3/1988 | Gallant et al. | 51/410 |
| 4,893,440 | 1/1990 | Gallant et al. | 51/436 |
| 4,950,160 | 8/1990 | Karst | 433/88 |
| 5,158,455 | 10/1992 | Bailey | 433/88 |
| 5,203,698 | 4/1993 | Blake et al. | 433/88 |
| 5,275,561 | 1/1994 | Goldsmith | 433/216 |
| 5,330,354 | 7/1994 | Gallant | 433/88 |
| 5,334,016 | 8/1994 | Goldsmith et al. | 433/29 |
| 5,334,019 | 8/1994 | Goldsmith et al. | 433/88 |
| 5,350,299 | 9/1994 | Gallant | 433/88 |
| 5,525,058 | 6/1996 | Gallant et al. | 433/88 |
| 5,618,177 | 4/1997 | Abbott | 433/88 |

OTHER PUBLICATIONS

W.H. McGehee, et al, A Textbook of Operative Dentistry, 1956, pp. 266–273.
Bonner, Phillip, Air Abrasion: The New "Drill–Less" Dentistry, Denistry Today, Sep. 1997 issue, pp. 58–65.
Goldstein, Ronald, et al., Air–Abrasive Technology: Its New Role in Restorative Dentistry, JADA, vol. 15, May 1994, pp. 551–557.

*Primary Examiner*—John J. Wilson
*Attorney, Agent, or Firm*—Douglas J. Hura; James B. Bieber

[57] ABSTRACT

A system for treating teeth and associated tooth structure using a pressurized air propellant mixed with abrasive material includes a manifold which defines air passages leading from the pressurized air source to dispensing chambers which hold the abrasive material. The manifold further provides a convenient structure for mounting a number of the system components. The manifold simplifies assembly of the system and improves the integrity of air passages within the system. The air abrasion system also has a mixing block and continuous purge feature which eliminate crosstalk and backflow problems when switching between abrasive materials. Evacuation apparatus incorporating a cyclone separator is integrally provided with the system which requires minimal regular maintenance and maximizes suction flow through the apparatus. A boost feature of the system is provided to selectively increase the ratio of abrasive material to air in an air-abrasive material mixture, thereby increasing the rate of tooth reduction, without requiring additional air pressure.

13 Claims, 5 Drawing Sheets

Fig_2

AIR ABRASION SYSTEM FOR USE IN DENTAL PROCEDURES

FIELD OF THE INVENTION

The present invention generally relates to systems used to perform dental procedures, and more particularly relates to systems for reducing teeth and associated structures.

BACKGROUND OF THE INVENTION

Dental procedures often require the dentist to remove decay from a tooth. The removal of tooth decay is commonly known as tooth reduction and may involve cutting, excavating, or etching of the enamel and dentin layers of the tooth. During these procedures, the dentist often must also remove all or part of associated tooth structures such as fillings, crowns, caps, composites, and the like.

Previously, dentists have used drills to reduce teeth. Drills, however, generate heat, vibration, and noise which cause discomfort in the patient. In addition, the dentist cannot precisely observe the progress of the drill as it cuts the tooth, increasing the likelihood that the drill may inadvertently cut through the dentin layer and into the sensitive pulp layer of the tooth, causing acute pain in the patient. As a result, anesthesia is typically used during tooth reductions performed using a drill.

More recently, air abrasion techniques have been used as a substitute for drilling. Air abrasion systems generally introduce abrasive material to a pressurized jet of air which is then directed toward the appropriate tooth area of the patient. Similar to sand-blasting, the pressurized air causes the abrasive material to strike the tooth at a sufficient velocity to remove a surface layer of the tooth. Air abrasion does not create the heat, vibration, and noise problems associated with drills. Furthermore, the dentist may more precisely control the area and depth of tooth material being removed, thereby reducing the amount of pain to the patient and often eliminating the need for anesthesia.

It has been found that different abrasive materials are more suited for particular dental procedures. For example procedures requiring relatively large amounts of tooth material to be removed can be performed more quickly with larger size abrasive particles. Procedures requiring relatively small amounts of tooth removal, and perhaps a greater degree of precision, are better performed with a smaller abrasive particle size. Accordingly, air abrasion systems are known, such as the apparatus described in Goldsmith et al., U.S. Pat. No. 5,334,019, which have a plurality of chambers. Each chamber in such a system supplies a different abrasive material. An air abrasion system which delivers more than one size particle allows the dentist to perform a full range of dental procedures by merely selecting the appropriate particle size.

Unfortunately, conventional air abrasion systems do not effectively switch between different particle sizes. When a conventional system stops delivering abrasive material to the patient, some of the abrasive material remains in the system, hose, and hand piece. The residual material restricts flow through the system so that, when the system subsequently attempts to deliver more abrasive material, the system must also push the residual material out the hand piece. As a result of the additional load created by the residual material, the subsequent blast delivered by the system has relatively low velocity and does not effectively reduce the tooth.

Residual abrasive material is even more detrimental when the dentist switches between abrasive materials. In that situation, the subsequent blast delivered by the system not only has a low velocity, but also contains the previous abrasive material which may not be suited for the particular procedure being performed by the dentist. Initial delivery of the wrong abrasive material after switching is known as "crosstalk", and is a significant disadvantage when using conventional air abrasion systems.

A further problem with conventional abrasion systems is backflow of biological material into the dispensing chambers. The abrasion hand piece is placed inside the patient's mouth during dental procedures. When abrasive material is not being delivered by the abrasion system, air pressures in the system allow biological material, such as blood, saliva, and portions of tooth, from the patient to flow back through the hand piece and hose and into the abrasion system. It is possible for the backflow material to reach the dispensing chambers, thereby clogging powder delivery and presenting a potential health risk to subsequent patients.

A significant problem with typical abrasion systems is clogging of the abrasive material due to moisture in the system. Abrasion systems typically deliver an abrasive powder material from a dispensing chamber through small diameter tubing. These systems are further typically connected to a compressor for supplying pressurized air to the chamber. The air supplied by the compressor has a water content which passes through the compressor and into the chambers. The moisture from the air, however, causes particles of abrasive powder to clump, thereby clogging the system.

Abrasion systems are known which use heating apparatus to address the moisture problem. The heating apparatus is used to increase the temperature in the system, thereby drying the abrasive powder. Such systems are inadequate, however, in that the moisture returns to the powder when the system subsequently cools or undergoes a pressure change. Furthermore, such systems require a start-up period during which the heating apparatus warms before the system may be used.

Conventional air abrasion systems further have an overly high number of fittings and tubing sections which form passages for the pressurized air through the system. The number of fittings increases the difficulty and amount of time needed to assemble the systems and introduces a number of potential air leaks.

An additional problem with the use of air abrasion systems is the efficient evacuation of used or spent abrasive material. After impacting upon the tooth, the abrasive material either collects in the patient's mouth or deflects back out into the area surrounding the patient's mouth. Conventional methods for collecting spent abrasive material typically involve a vacuum-type system having a filter. The filter, however, rapidly clogs with abrasive material and other larger debris such as portions of tooth and gum material. The clogged filter restricts air flow through the system, thereby lowering suction capacity. Conventional abrasion systems further require frequent filter changes due to the clogging.

SUMMARY OF THE INVENTION

A general aim of the present invention is to provide an air abrasion system which is easy to assemble and has air passages with improved integrity.

It is also an object of the present invention to provide an air abrasion system which eliminates crosstalk when used with multiple abrasive materials.

It is a related object of the present invention to provide an air abrasion system which prevents backflow of material into the system from the connected hand piece.

It is a further object of the present invention to provide an air abrasion system in which the dentist may immediately increase the rate of tooth removal without increasing air pressure.

Yet another object of the present invention is to provide an air abrasion system which both delivers and collects the abrasive powder used by the system, but has minimal regular maintenance.

Still another object of the present invention is to provide an air abrasion system which prevents moisture from entering the system.

In light of the above, the present invention provides an improved air abrasion system which includes a manifold constructed and arranged to reduce the number of parts needed to assemble the system and for improving the integrity of pressurized air passages in the system. The manifold provides the entire air passage between the air supply and dispensing chambers and a portion of the boost and purge passages. The manifold eliminates the need for tubing and associated fittings to create the air passages which not only simplifies assembly but reduces the number of potential air leaks in the system.

The present invention also provides an improved air abrasion system having a mixing block which, in combination with the continuous purge feature, eliminates crosstalk and backflow problems. The mixing block has multiple inlet ports to handle multiple abrasive materials. The mixing block further has a purge port connected to a purge passage through which air is continuously fed. Each port in the mixing block has an associated bore. The bores have a consistent diameter which reduces the dead volume through the mixing block. As a result, once the system stops delivering abrasive material to the abrasion hand piece, the purge air will clear the hose and hand piece connected to the system of any residual abrasive material. The continuous purge flow further prevents material from backing up through the hand piece and hose to enter the system.

It is also a feature of the present invention to provide an air abrasion system with a boost setting which immediately increases the rate of tooth removal without requiring additional air pressure. In the boost setting, the amount of air delivered to the mixing block is reduced, thereby increasing the ratio of abrasive material in the mixture delivered by the system. The higher proportion of abrasive material increases the rate of cutting performed by the system.

It is yet another feature of the present invention to provide a filter between the pressurized air source and air inlet line for preventing clogging of abrasive material in the system. The filter effectively removes moisture from the air delivered to the system without using heating apparatus, thereby avoiding long warm-up periods for the system.

It is still another feature of the present invention to provide an air abrasion system with integral evacuation capabilities requiring little maintenance. The air abrasion system houses a vacuum pump and filter components attached to an evacuation hand piece which collects spent abrasive material from the mouth area of the patient. A cyclone separator is located before the filter for removing larger debris from the evacuation air stream. The larger debris separated by the cyclone collect in a cup which is easily emptied and replaced on the cyclone. By removing the larger debris, the filter does not become clogged as quickly and therefore does not have to be frequently replaced.

In certain embodiments, it is a feature of the present invention to provide an air abrasion system which has an integral pressurized gas source.

These and other objects and advantages of the invention will become more apparent from the following detailed description when taken in conjunction with the accompanying drawings.

Figure 1:
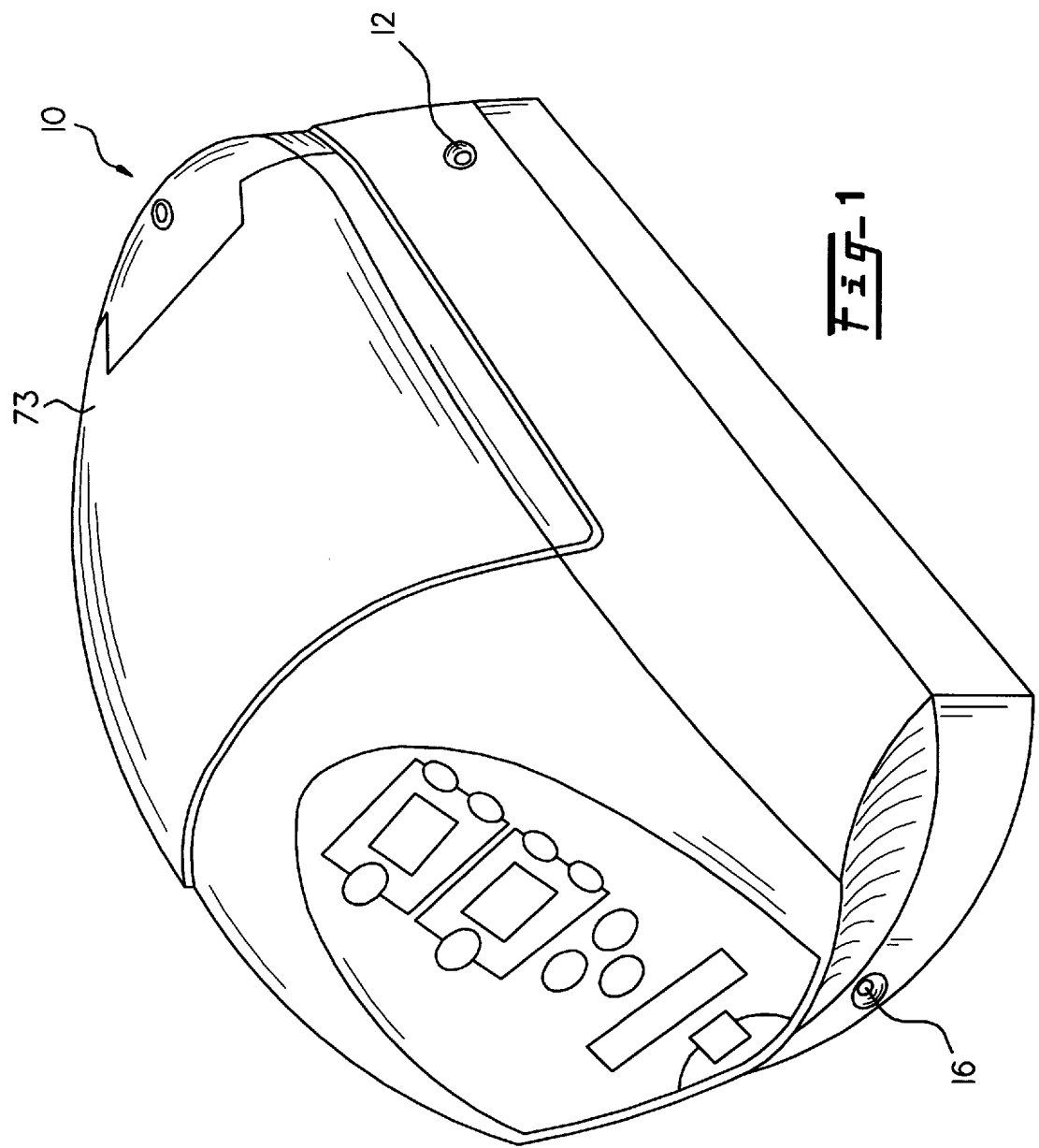
FIG. 1 is a perspective view of an air abrasion system in accordance with the present invention for placement on a countertop.

While the invention is susceptible of various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions and equivalents falling within the spirit and scope of the invention as defined by the appended claims.

DETAILED DESCRIPTION OF THE PREFERRED EMBODIMENTS

Figure 2:
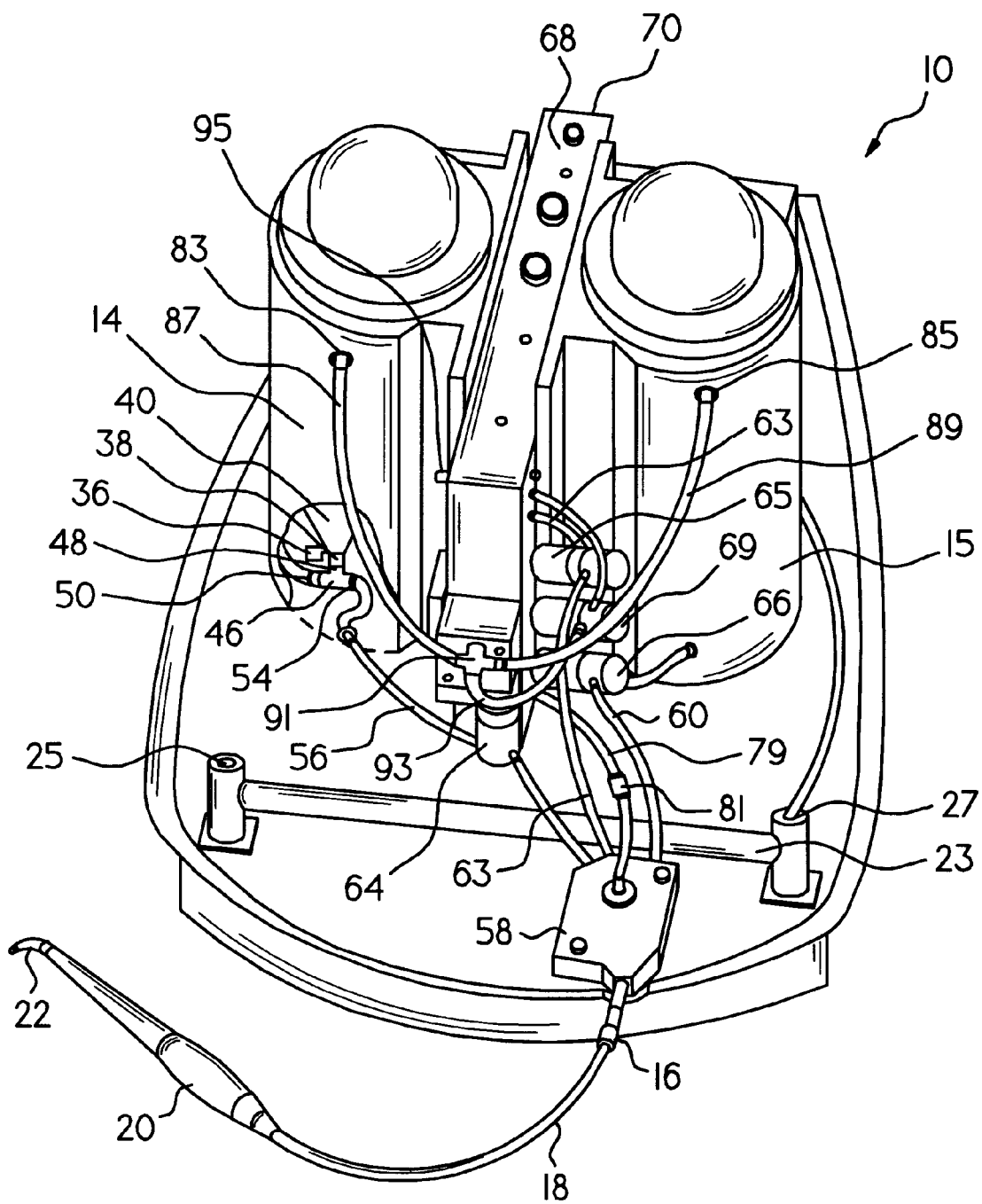
FIG. 2 is a perspective view of the components of the air abrasion system shown in FIG. 1.

Referring now to the drawings, FIG. 1 shows a countertop version of an air abrasion system 10 in accordance with the present invention. The system 10 is connected to a hose 18 and abrasion hand piece 20, as shown in FIG. 2. The countertop system 10 is connected at air connection 12 to a pressurized fluid source (not shown) which preferably supplies pressurized propellant gas. While air, $CO_2$, and other gases may be used as the propellant in accordance with the present invention, for the sake of simplicity the system is described below as using air as the propellant, unless specifically indicated otherwise. The system mixes pressurized air with abrasive material and passes the mixture through an outlet connection 16 for delivery to the hose 18 and hand piece 20. A tip 22 of the hand piece 20 is inserted inside the mouth of a patient and aimed at the tooth structure, whereupon the abrasive material strikes the tooth of the patient and removes a surface layer of the tooth. Any abrasive particles may be used according to the invention as long as they are fine enough to be fluidized and delivered in a propellant gas. Aluminum oxide is the generally preferred material for the abrasive treatment of teeth. For the sake of simplicity, the invention is described below in the context of delivering an abrasive material, and all such materials and particles are referred to below as abrasive "powder".

In greater detail, pressurized gas, preferably air, from the outside source first passes through an inlet filter 23 for removing moisture from the air (FIG. 2). The inlet filter 23 has an inlet 25 connected to the gas source and an outlet 27. The inlet filter 23 is preferably of the hollow fiber membrane type and is sized for the air flows typically required through the system. The inlet filter 23 prevents moisture from entering the system to thereby avoid clogging of abrasive material associated with moisture.

Figure 3:
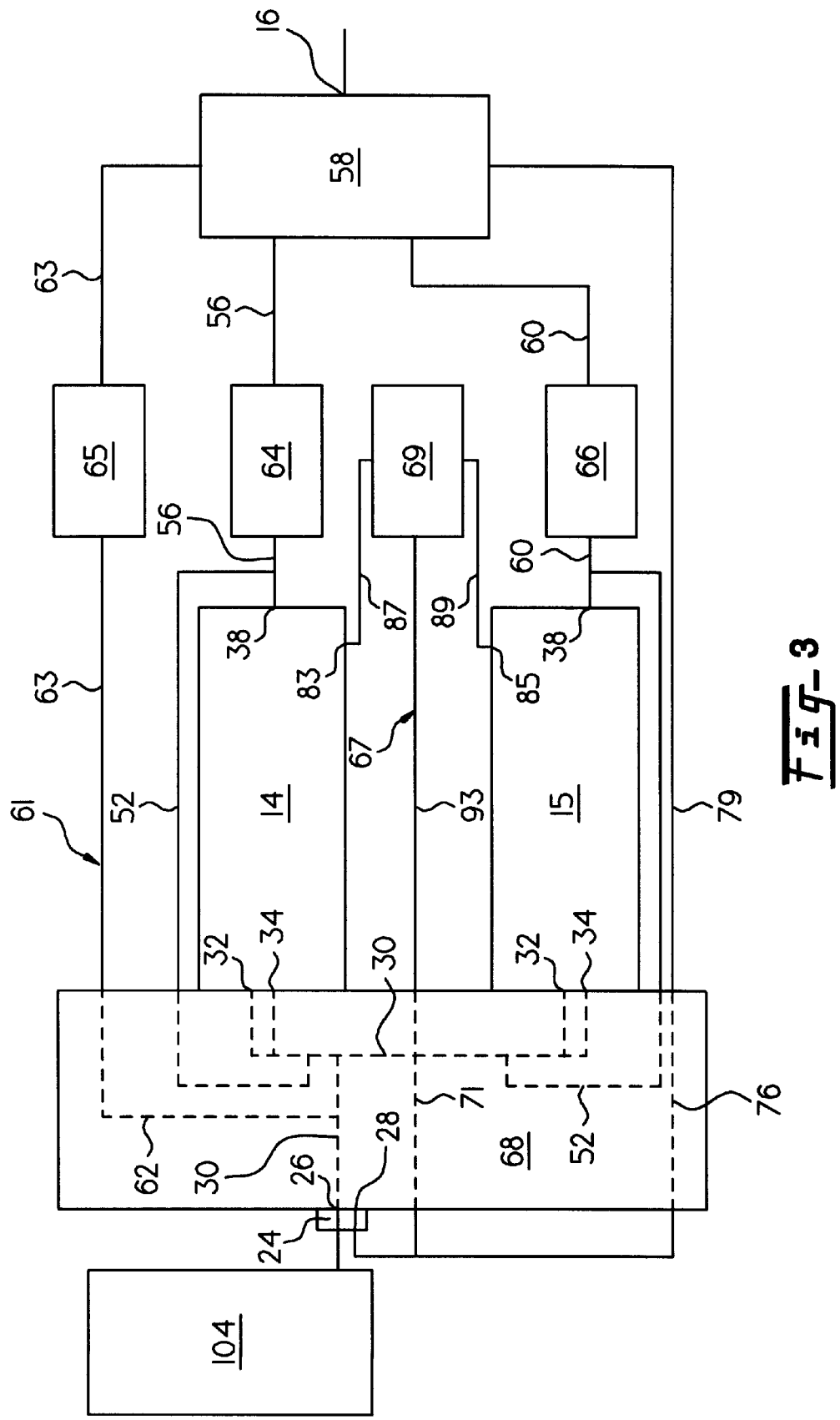
FIG. 3 is a schematic representation of the air flow passages of the air abrasion system of FIG. 1.

From the inlet filter 23, the pressurized air next passes through a regulator 24 (shown schematically in FIG. 3)

connected to the air connection 12, as best shown in FIG. 2. The regulator 24 discharges pressurized air through first and second outlet ports 26, 28. The first outlet port 26 is fluidly connected to a pair of dispensing chambers 14, 15 by a chamber inlet air passage 30. Air from the second outlet port 28 of the regulator 24 travels through a purge passage 32 to ultimately provide the purge feature of the air abrasion system 10, as described more fully below.

The dispensing chambers 14, 15 are provided for storing and releasing the abrasive material into the propellant gas stream. According to the illustrated embodiment, each dispensing chamber 14, 15 has upper and lower air inlet ports 32, 34 attached to the chamber inlet air passage 30 (FIG. 3). At the bottom of each dispensing chamber is a funnel 40 with attached vibrating motor 36 for directing abrasive powder through a powder outlet port 38 of the chamber. The motor 36 vibrates the funnel 40 so that abrasive powder in the funnel is fluidized and more easily dispensed through the powder outlet port 38 without clogging, as described more fully in Abbott, U.S. Pat. No. 5,618,177, incorporated herein. The funnel 40 has a top edge which engages the inside surface of the dispensing chamber and narrows to a lower edge disposed near the powder outlet port 38. The funnel 40 is made of a resilient material which is susceptible to deformation.

It will therefore be appreciated that a pressure differential across the cone may create a force sufficient to deform the funnel 40 and, accordingly, the upper and lower inlet ports 32, 34 of the dispensing chambers 14, 15 are positioned on opposite sides of the directing cone 40 to thereby equalize the pressure in the dispensing chamber.

A T-block 46 is connected to the powder outlet port 38 of each dispensing chamber 14, 15 for combining abrasive powder with pressurized gas. With respect to dispensing chamber 14, it will be seen that the T-block 46 has a first inlet arm 48 attached to the powder outlet port 38. The T-block 46 has a second inlet arm 50 which communicates with a feed air passage 52 which branches off of the chamber inlet air passage 30 (FIG. 3). A mixture of abrasive powder from the powder outlet port 38 of the dispensing chamber 14 and pressurized gas from the feed air passage 52 is directed through an outlet arm 54 of the T-block 46. The outlet port 54 of the T-block 46 is attached to a first air-powder passage 56 formed of flexible tubing. The first air-powder passage 56 terminates at a mixing block 58, at which point the air-powder mixture is combined with additional pressurized air and discharged out the outlet connection 16, as described more fully below.

Dispensing chamber 15 is assembled similar to the above-described dispensing chamber 14. The powder outlet port 38 of dispensing chamber 15 is connected to a first inlet arm 48 of T-block 46. The second inlet arm 50 of the T-block 46 is attached to the same feed air passage 52 noted above. The outlet arm 54 of the T-block 46 is attached to a second air-powder passage 60 which also ultimately terminates at the mixing block 58.

At this point, it will be appreciated that the air abrasion system of the present invention is capable of delivering different abrasive powders. The dispensing chambers 14, 15 share the chamber inlet air passage 30 and feed air passage 52. Each chamber, however, has a separate powder outlet port 38, T-block 46, and air-powder passage. The dispensing chambers 14, 15 are filled with different abrasive powders. For example, chamber 14 holds aluminum oxide particles having diameters of about 27 microns and chamber 15 holds aluminum oxide particles having diameters of about 50 microns. The system is operated to selectively deliver abrasive powder from one chamber at a time, thereby allowing the dentist to use an abrasive material better suited for the dental procedure to be performed.

In accordance with certain aspects of the present invention, a boost air line 61 runs from the chamber inlet air passage 30 to the mixing block 58 for selectively increasing the rate of tooth reduction at a given air pressure. As schematically shown in FIG. 3, the boost air line 61 branches from the chamber inlet air passage 30 near the upper inlet ports 32 of the dispensing chambers 14, 15 and terminates at the mixing block 58. Accordingly, it will be appreciated that pressurized air from the chamber inlet air passage 30 passes through the boost passage 62 and is ultimately directed to the mixing block 58 and provides additional pressurized air for mixing with the abrasive powder. A boost passage 62 forms a portion of the boost air line 61. Flexible tubing 63 connects the boost passage 62 to the mixing block 58 (FIG. 2). A pinch valve 65 is located along the flexible tubing 63 for controlling air flow through the boost passage.

In operation, the boost line is used to selectively increase the rate of tooth reduction. Under normal operating conditions, the pinch valve 65 is open and air travels through the boost air line 61 to the mixing block 58, where the air is mixed with an air-powder mixture from one of the dispensing chambers 14, 15. This new mixture exits the outlet connection 16 and travels through the hose 18 to be directed by the hand piece 20. When the boost feature is selected, the pinch valve 65 is closed and additional pressurized air is not added to the air-powder mixture at the mixing block 58.

With the reduction of gas flow, the ratio of abrasive powder in the air-powder mixture is increased, thereby increasing the cutting rate of the system. In this manner, the air abrasion system of the present invention is able to immediately increase the cutting rate without requiring an increase in gas pressure.

Pinch valves 64, 66 control the flow of abrasive powder from the dispensing chambers 14, 15 through the first and second air-powder passages 56, 60 to the mixing block 58. When the pinch valves are open, the pressurized air pushes the abrasive powder through the air-powder passage toward the mixing block. When the pinch valves are closed, abrasive powder is prevented from reaching the mixing block. As illustrated in FIG. 3, each dispensing chamber 14, 15 has an associated pinch valve 64, 66. The pinch valves 64, 66 are independently actuated so that when pinch valve 64 is open, pinch valve 66 is closed, and vice versa. As a result, the abrasive powder from a single chamber is delivered during operation of the system.

In accordance with significant aspects of the present invention, a manifold 68 is provided which improves the integrity of the air passages between the regulator 24 and the dispensing chambers 14, 15 and T-blocks 46. As best shown in FIG. 2, the manifold 68 is formed as a generally rectangular plate disposed between the dispensing chambers 14, 15. The regulator 24 is attached to a rear face 70 of the manifold 68, while a dispensing chamber is attached to each side of the manifold. A number of bores are formed through the manifold which define various of the air passages described above. As best shown schematically in FIG. 3, the chamber inlet air passage 30 extends from the first outlet port 26 of the regulator to the upper and lower inlet ports 32, 34 of the dispensing chambers 14, 15. The feed air passage 52 branches off of the chamber inlet air passage 30 and leads to the T-blocks 46. Also branching off the chamber inlet air passage 30 is the boost passage 62 located near the upper inlet ports 32. A purge passage 76 also extends through the manifold 68, is connected to the second outlet port 28 of the regulator 24 on an inlet side and is fluidly connected to the mixing block 58 on an outlet side by flexible tubing 79. By having the manifold 68 provide the entire chamber inlet air passage 30 and feed air passage 52, the system of the present invention reduces the number of parts for assembly and potential air leaks.

The manifold 68 also provides a convenient structure onto which a number of the components of the system are mounted. As illustrated in FIG. 2, the dispensing chambers 14, 15 are mounted on opposite sides of the manifold 68. The pinch valves 64, 66 for controlling the flow of abrasive powder through the first and second air-powder passages 56, 60 and pinch valve 65 controlling the boost line 61 are also affixed to the manifold 68. The manifold further has attached thereto the regulator 24 so that the first outlet port 26 of the regulator is directly adjacent the chamber inlet air passage 30. The manifold 68, in accordance with the present invention, therefore provides structure for mounting a number of components, thereby simplifying assembly of the system.

Figure 4:
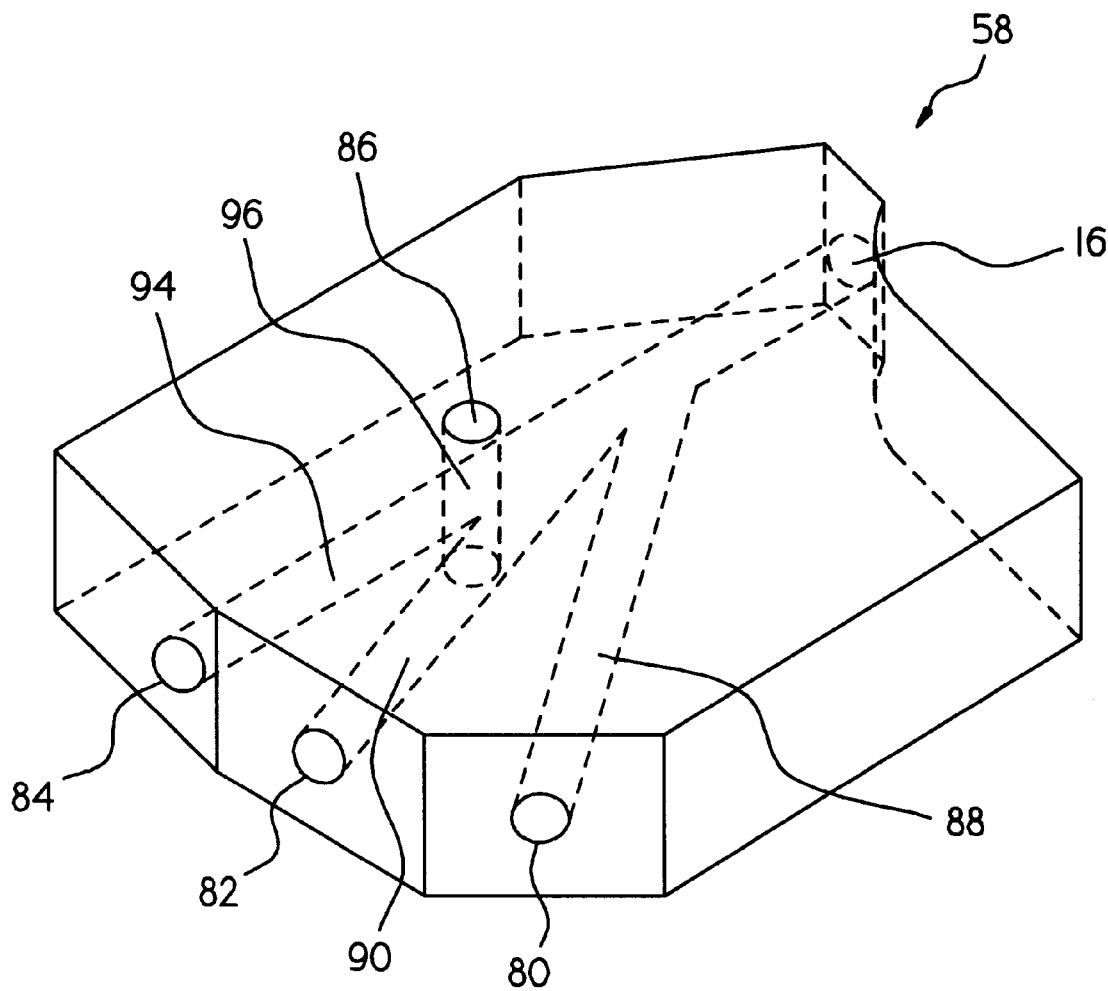
FIG. 4 is an enlarged perspective view of a mixing block in accordance with the present invention.

It will now be appreciated that the mixing block 58 of the present invention, in combination with the continuous purge feature, eliminates the crosstalk problem seen in convention air abrasion systems. The mixing block 58 is located near the front of the system housing and provides the outlet connection 16 for attachment to the hose 18 and abrasion hand piece 20. The mixing block 58 is connected with flexible hosing to the boost passage 62, purge passage 76, and first and second air-powder passages 56, 60 (FIG. 3). As shown in FIG. 4, the mixing block 58 is formed from a solid piece of metal through which converging passages are bored. The mixing block has a first powder inlet port 80, a boost inlet port 82, a second powder inlet port 84, a purge inlet port 86, and the outlet connections 16. As best shown in FIG. 4, the second powder inlet port 84 is substantially aligned with the outlet connection 16. A first powder bore 88 extends between the first powder inlet port 80 and the outlet connection 16. The boost inlet port 82 is disposed at an angle to the first powder inlet port 80 and has an associated boost bore 90 which intersects a purge inlet bore 96. The second powder inlet port 84 is disposed at a greater angle than the boost inlet port 82 from the first powder inlet port 80 and has associated therewith a second powder bore 94 which intersects the first powder inlet bore 88 and boost bore 90. The purge inlet port 86 is disposed normal to the boost inlet port 82 and has the purge bore 96 associated therewith which intersects the boost bore 90 at approximately a right angle. In the preferred embodiment, the diameters of the bores are kept consistent through the mixing block 58 to thereby reduce dead volume. As a result, the amount of residual material gathering in the mixing block 58 due to dead volume is minimized.

In accordance with certain aspects of the present invention, the air abrasion system continually purges air through the purge passage when the system is switched on. As described above, the purge passage 74 is connected to the second outlet port 28 of the regulator 24. An air restrictor/filter 81 (FIG. 2) is located in the flexible tubing 79 for controlling air pressure through the purge line and filtering the purge air flow. As noted above, the purge bore 96 in the mixing block 58 ties into the boost bore 90 which directs purge air toward the outlet connection 16. With reference to FIG. 4, it will appreciated that the purge air continuously pushes residual abrasive powder through the mixing block 58 and out the outlet connection 16. When the air abrasion system 10 is connected to a flexible hose 18 and abrasion hand piece 20, the purge air also continuously purges the hose 18 and hand piece 20 of residual abrasive powder. The continuous purge also prevents backflow of material through the hand piece and hose into the system.

The air abrasion system 10 may also include a vent line 67 for reducing pressure levels in the dispensing chambers 14, 15. Regardless of the gas source used, the pressure levels in the dispensing chambers 14, 15 ranges from about 40 to about 120 psi or more. When opening a chamber to, for example, refill it with abrasive powder, the elevated pressure in the chamber will cause any remaining abrasive powder to exit the chamber at a velocity sufficient to injure a person standing near the chamber. To avoid such a situation, the present invention provides the vent line 67 for relieving pressure in the chambers. As best shown in FIG. 2, vent ports 83, 85 are located on the first and second dispensing chambers 14, 15 for relieving pressure from the chambers. First and second vent tubes 87, 89 are attached to the vent ports 83, 85 and lead to a tee 91. The tee 91 discharges into a common vent tube 93 which passes through a pinch valve 69 and is ultimately connected to a vent passage 71 in the manifold 68 (FIG. 3). A filter 95 is mounted on the manifold at the outlet of the vent passage 71 through which vent air discharges to atmosphere.

In operation, the pinch valve 69 for the vent line 67 is normally closed to pinch the common vent tube 93, thereby restricting flow through the vent line 67 and allowing pressure to build in the dispensing chambers 14, 15. When an appropriate signal is delivered, the pinch valve 69 opens to relieve pressure in the chambers. Once the pressure is lowered, the chambers may be accessed without risk of injury from abrasive powder or other projectiles from the chambers. In the most preferred embodiment, the signal to the pinch valve 69 is interlocked to the position of a housing cover 73 (FIG. 1) so that, when the cover 73 is lifted, the system vents pressure from the dispensing chambers 14, 15.

Figure 5:
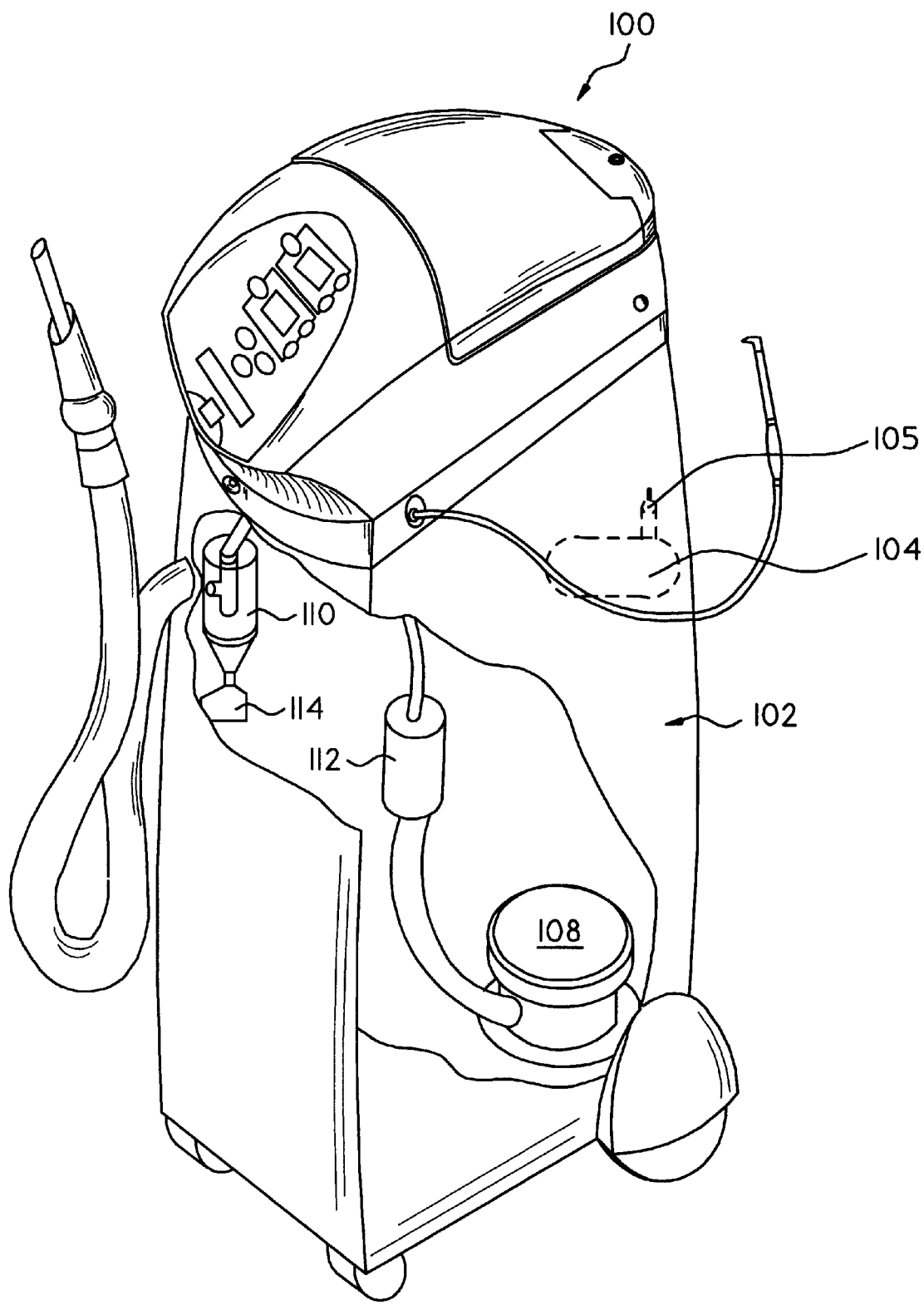
FIG. 5 is a partly schematic perspective view of a portable air abrasion system having integral pressurized gas source and evacuation apparatus.

FIG. 5 illustrates an alternative embodiment of the present invention in which an air abrasion system is portable and completely self contained. The portable air abrasion system 100 has a lower compartment 102 which houses additional components to provide an integral air supply and evacuation. As best illustrated in FIG. 6, the portable system 100 incorporates the pressurized gas source 104. The pressurized gas source may take the form of a compressor, which delivers pressurized air, or a pressurized bottle of $CO_2$. With either source, a sufficient amount of pressurized gas is provided with the air abrasion system, thereby removing the need to hook the system up to an outside source of pressurized gas. The pressurized gas source has an outlet 105 which is fluidly connected to the air filter 23 (FIG. 1).

The portable air abrasion system 100 further includes apparatus for evacuating excess abrasive powder from the mouth area of the patient after treatment. As shown in FIG. 5, the evacuation apparatus includes a vacuum pump 108 to create suction air flow. The pump 108 pulls evacuation air through a cyclone separator 110 and a filter 112. In the preferred embodiment, the filter 112 is a HEPA filter. The cyclone separator 110 removes debris having greater mass than air from the suction air flow. The debris removed by the cyclone separator 110 collects in a removable container 114 attached to the bottom of the cyclone separator. The container 114 can easily be removed, emptied, and re-installed onto the cyclone separator 110. Accordingly, the cyclone separator 110 collects the abrasive powder, water, and other debris from the suction air flow. The filter 112 collects any debris not removed by the cyclone separator.

The cyclone separator 110 maximizes the suction capacity of the evacuation apparatus and increases the filter life. The cyclone separator 110 does not restrict air flow, no matter how much debris it removes. As a result, the evacuation apparatus operates at a higher suction capacity for a longer period of time. Furthermore, since most of the debris is removed from the suction flow by the cyclone separator 110, the life of the filter is increased.

The integral evacuation system of the present invention conveniently eliminates the need for a separate evacuation system. This advantage takes on greater significance when the only other available evacuation is the office system. Office systems typically have lower suction flow rates and therefore a lower capture ratio. Such systems also do not have cyclone separators and therefore easily clog from air abrasive procedures. Furthermore, typical office evacuation systems use filters which are easily damaged by abrasive material.

The portable system 100 incorporates the same manifold 68 and mixing block 58 as the countertop system 10, and are sufficiently described above.

From the foregoing, it will be apparent that the present invention brings to the art a new and improved air abrasion system with improved pressurized air passage integrity and more effective switching between abrasive materials without crosstalk. The air abrasion system incorporates a manifold for providing air passages between the pressurized gas source and the dispensing chambers. A plurality of bores in the manifold define the passages. The mixing block receives an air-powder mixture from either dispensing chamber and adds air through a boost port to the mix. The air from the boost port may be shut off, thereby creating a boost condition in which the ratio of abrasive material to air is increased. A purge line ties into the boost port and continuously purges air through the mixing block and attached hose and hand piece. Accordingly, when the dentist selects a new abrasive material to be delivered by the system, the mixing block, hose, and hand piece have already been purged of any previous residual material. As a result, the dentist may quickly and conveniently switch between abrasive materials without experiencing crosstalk.

What is claimed is:

1. An abrasion system for delivering a mixture of pressurized gas and abrasive powder for use in dental procedures, the air abrasion system adapted to be attached to a pressurized gas source and a hose connected to a an abrasion hand piece, the system comprising the combination of:

a first dispensing chamber having a reservoir for holding a supply of abrasive powder, an inlet port adapted for fluid communication with the pressurized gas source, a powder outlet port, and motor means for advancing abrasive powder through the powder outlet port;

a mixing block having a first powder inlet port fluidly connected to the powder outlet port of the first dispensing chamber, and a purge port adapted for fluid connection to the pressurized gas source, wherein the first powder inlet port and purge port have associated therewith a first powder bore and purge bore, respectively, extending through the mixing bock and converging to form a common outlet connection adapted for releasable attachment to the hose;

wherein pressurized gas is supplied to the purge port for continuous flow through the mixing block, hose, and hand piece;

further comprising a second dispensing chamber having a reservoir for holding a supply of abrasive power, an inlet port adapted for fluid communication with the pressurized gas source, a powder outlet port, and motor means for advancing abrasive powder through the powder outlet port; wherein the mixing block further includes a second powder inlet port fluidly connected to the powder outlet port of the second dispensing chamber, the first power inlet port having associated therewith a second powder bore extending through the mixing block and leading to the common outlet connection.

2. An abrasion system for delivering a mixture of pressurized gas and abrasive powder for use in dental procedures, the air abrasion system adapted to be attached to a pressurized gas source and a hose connected to a an abrasion hand piece, the system comprising the combination of:

a first dispensing chamber having a reservoir for holding a supply of abrasive powder, an inlet port adapted for fluid communication with the pressurized gas source, a powder outlet port, and motor means for advancing abrasive powder through the powder outlet port;

a mixing block having a first powder inlet port fluidly connected to the powder outlet port of the first dispensing chamber, and a purge port adapted for fluid connection to the pressurized gas source, wherein the first powder inlet port and purge port have associated therewith a first powder bore and purge bore, respectively, extending through the mixing bock and converging to form a common outlet connection adapted for releasable attachment to the hose;

wherein pressurized gas is supplied to the purge port for continuous flow through the mixing block, hose, and hand piece;

in which the mixing block further comprises a boost port with associated boost bore extending through the mixing block to converge with the first powder bore and purge bore, and a valve selectively controls delivery of the pressurized gas to the boost bore so that, when the valve is closed, the mixture of pressurized gas and abrasive powder has an increased proportion of abrasive powder.

3. The abrasive system of claim 2 in which the first powder bore extends linearly between the first powder inlet port and the outlet connection, and the boost bore intersects the first powder bore at an angle.

4. The abrasive system of claim 2 in which the first powder bore and purge bore have consistent diameters.

5. An abrasion system for delivering a mixture of pressurized gas and abrasive powder for use in dental procedures, the air abrasion system adapted to be attached to a pressurized air source and a hose connected to an abrasion hand piece, the system comprising the combination of:

a regulator having an air intake port sized for fluid connection to the pressurized air source, and first and second outlet ports;

a first dispensing chamber having a reservoir for holding a supply of abrasive powder, an inlet port fluidly connected to the first outlet port of the regulator by a chamber inlet air passage, a powder outlet port, and motor means for advancing abrasive material through the powder outlet port;

a first T-blocks attached to the first dispensing chamber and having a first inlet arm connected to the powder outlet port, a second inlet arm connected to a feed air passage branching from the chamber inlet air passage, and an outlet arm;

a mixing block having a first powder inlet port fluidly connected to the outlet arm of the first T-block by a first air-powder passage, a boost inlet port fluidly connected to a boost passage, a purge inlet port fluidly connected to the second outlet port of the regulator by a purge passage, and an outlet connection adapted to fit the hose leading to the abrasion hand piece; and a manifold onto which the dispensing chamber is mounted, the manifold providing the chamber inlet air, feed air, and a portion of the boost and purge passages.

6. The abrasion system of claim 5 further comprising integral evacuation apparatus adapted for use with an evacuation hose with attached evacuation hand piece, the evacuation apparatus including a vacuum pump having an inlet, a filter connected to the inlet of the vacuum pump, a cyclone separator connected upstream of the filter, and an evacuation port sized for connection to the evacuation hose.

7. The abrasion system of claim 5 in which pressurized gas continuously passes through the purge passage.

8. The abrasion system of claim 5 in which the pressurized gas source is integrally provided with the system.

9. The abrasion system of claim 8 in which the pressurized gas source is an air compressor.

10. The abrasion system of claim 8 in which the pressurized gas source is a bottle of compressed $CO_2$.

11. The abrasion system of claim 5 in which a valve selectively controls delivery of the pressurized gas to the boost bore so that, when the valve is closed, the mixture of pressurized gas and abrasive powder has an increased proportion of abrasive powder.

12. The abrasion system of claim 5 in which the first dispensing chamber further comprises a vent port attached to a vent tube which discharges to atmosphere, a vent valve selectively controlling flow through the vent tube, the vent valve relieving gas pressure in the dispensing chambers when open.

13. The abrasion system of claim 12 further comprising a housing cover providing access to the dispensing chambers, wherein the vent valve is interlocked with the position of the housing cover so that, when the housing cover is open, the vent valve opens.

* * * * *